United States Patent [19]

Hunkeler et al.

[11] 4,362,732

[45] Dec. 7, 1982

[54] DIAZEPINE DERIVATIVES AND THEIR USE

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 349,749

[22] Filed: Feb. 18, 1982

[30] Foreign Application Priority Data

Feb. 27, 1981 [CH] Switzerland .......................... 1342/81

[51] Int. Cl.³ .................... A61K 31/55; C07D 471/14
[52] U.S. Cl. ............................ 424/256; 260/239.3 T; 260/239.3 B
[58] Field of Search ................. 260/239.3 T; 424/256

[56] References Cited

U.S. PATENT DOCUMENTS 4,316,832  2/1982  Gerecke et al. ............. 260/239.3 T Primary Examiner—Robert T. Bond
Attorney, Agent, or Firm—Jon S. Saxe; Bernard S. Leon; Frank P. Hoffman

[57] ABSTRACT

There is presented imidazodiazepines of the formula

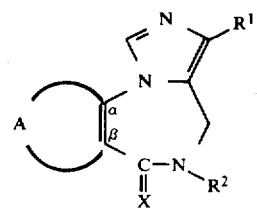

wherein A together with the two carbon atoms denoted as $\alpha$ and $\beta$ is a pyridine ring, X is an oxygen or sulphur atom, $R^1$ is hydrogen, halogen, lower alkyl, lower alkoxymethyl or the group—$COOR^3$ and $R^2$ and $R^3$ each are lower alkyl, and their pharmaceutically acceptable acid addition salts. The compounds are useful in the antagonization of the central-depressant, muscle relaxant, ataxic, blood pressure-lowering and respiratory-depressant properties of 1,4-benzodiazepines which have tranquillizing activity, for example as antidotes in the case of intoxications with 1,4-benzodiazepines which have tranquillizing activity.

Also presented are methods to produce such imidazodiazepines.

12 Claims, No Drawings

DIAZEPINE DERIVATIVES AND THEIR USE

DESCRIPTION OF THE INVENTION

The present invention is concerned with imidazodiazepines. More particularly, the invention is concerned with imidazodiazepines of the formula

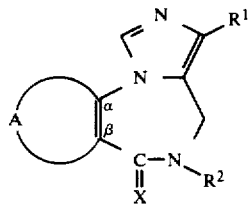

wherein A together with the two carbon atoms denoted as $\alpha$ and $\beta$ is a pyridine ring, X is an oxygen or sulphur atom, $R^1$ is hydrogen, halogen, lower alkyl, lower alkoxymethyl or the group—$COOR^3$ and $R^2$ and $R^3$ each are lower alkyl, and pharmaceutically acceptable acid addition salts thereof.

These compounds are novel and possess valuable pharmacodynamic properties. They are accordingly suitable for use in the control or prevention of illnesses.

Objects of the present invention are compounds of formula I and pharmaceutically acceptable acid addition salts thereof per se and as pharmaceutically active substances, the manufacture of these compounds and intermediates for the manufacture of these compounds, medicaments containing a compound of general formula I or a pharmaceutically acceptable acid addition salt thereof and the manufacture of such medicaments.

The symbol A denotes together with the two carbon atoms denoted as $\alpha$ and $\beta$ the group

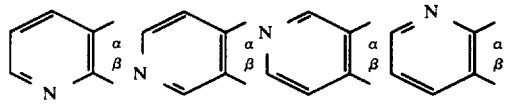

The term "lower alkyl" denotes saturated hydrocarbon groups, which can be straight-chain or branched-chain, containing at most 7, preferably at most 4, carbon atoms such as methyl, ethyl, isopropyl, t-butyl and the like. The term "lower alkoxymethyl" embraces groups such as methoxymethyl, ethoxymethyl and the like. The term "halogen" signifies fluorine, chlorine, bromine and iodine.

$R^1$ preferably is chlorine or the group—$COOR^3$ in which $R^3$ preferably is methyl, ethyl, isopropyl or t-butyl. In an especially preferred embodiment, $R^1$ is the group—$COOR^3$ in which $R^3$ is ethyl or t-butyl.

The symbol A preferably is the group (a), (b) or (d), with the group (b) being especially preferred. $R^2$ preferably is methyl. The symbol X preferably is an oxygen atom.

A quite especially preferred compound of formula I is t-butyl 5,6-dihydro-5-methyl-6-oxo-4H-imidazo[1,5-a]-pyrido[3,4-f][1,4]diazepine-3-carboxylate.

Other compounds of formula I which are especially preferred are:

t-Butyl 5,6-dihydro-5-methyl-6-oxo-4H-imidazo[1,5-a]-pyrido[2,3-f][1,4]diazepine-3-carboxylate, ethyl 5,6-dihydro-5-methyl-6-oxo-4H-imidazo[1,5-a]-pyrido[2,3-f][1,4]diazepine-3-carboxylate, 3-chloro-4,5-dihydro-5-methyl-6H-imidazo[1,5-a]-pyrido[2,3-f][1,4]diazepin-6-one, t-butyl 5,6-dihydro-5-methyl-6-oxo-4H-imidazo[1,5-a]-pyrido[3,2-f][1,4]diazepine-3-carboxylate and ethyl 5,6-dihydro-5-methyl-6-oxo-4H-imidazo[1,5-a]-pyrido[3,4-f][1,4]diazepine-3-carboxylate.

The imidazodiazepines of formula I and their pharmaceutically acceptable acid addition salts can be manufactured in accordance with the invention by (a) reacting a compound of the formula

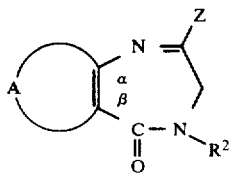

wherein A and $R^2$ are as above and Z is a leaving group, in the presence of a base with an isocyanoacetic ester of the formula $$CN-CH_2-COOR^3 \qquad (III)$$

wherein $R^3$ is as above, or (b) decarboxylating a carboxylic acid of the formula

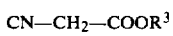

wherein A, X and $R^2$ are as above or (c) halgenating a compund of the formula

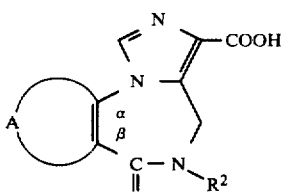

wherein A, X and $R^2$ are as above, or (d) etherifying a compound of the formula

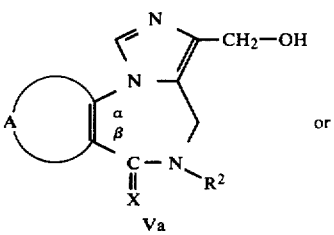

-continued

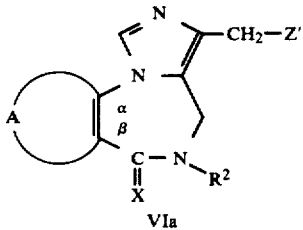

wherein A, X and R² are as above and Z' is a leaving group, with an alkylating agent yielding a lower alkyl group in the case of a compound of formula Va or with a lower alcohol in the case of a compound of formula VIa, or (e) cleaving off under reductive conditions the leaving group denoted by Z' in a compound of the formula

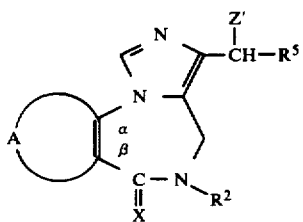

wherein A, X, Z' and R² are as above and R⁵ is hydrogen or lower alkyl, or (f) trans-esterifying a compound of the formula

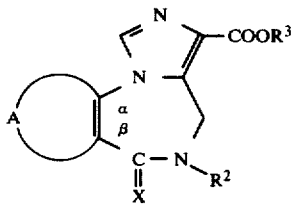

wherein A, X, R² and R³ are as above, or (g) converting the carbonyl group in a compound of the formula

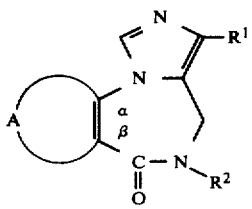

wherein A, R¹ and R² are as above, into the thiocarbonyl group, and (h) if desired, converting a compound of formula I obtained into a pharmaceutically acceptable acid addition salt.

In accordance with process variant (a), compounds of formula I can be manufactured from compounds of formula II and isocyanoacetic esters of formula III. The leaving group denoted by Z in formula II is, for example, a readily cleavable phosphinyl group, e.g. a group of the formula

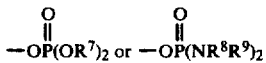

wherein R⁷ is lower alkyl and R⁸ and R⁹ each are lower alkyl, allyl, phenyl or substituted phenyl or R⁸ and R⁹ together with the nitrogen atom are an unsubstituted or substituted heterocyclic ring with 3-8 members (such as morpholine), a halogen atom, an alkylthio group, an aralkylthio group, a N-nitrosoalkylamino group, an alkoxy group, a mercapto group and the like (when Z is a mercapto group, then the corresponding compound of formula II is the iminothiol form of the corresponding thiolactam). The reaction of a compound of formula II with a compound of formula III is carried out in an inert solvent such as dimethylformamide, hexamethylphosphoric acid triamide, dimethyl sulphoxide, tetrahydrofuran or any other suitable organic solvent and in the presence of a base which is sufficiently strongly basic to form the anion of the isocyanoacetic ester of formula III. Suitable bases are alkali metal alkoxides such as sodium methoxide or potassium t-butoxide, alkali metal hydrides such as sodium hydride, alkali metal amides such as lithium amide or lithium diisopropylamide, tertiary amines such as triethylamine, and the like. The reaction is conveniently carried out at a temperature between about −40° and about room temperature.

In accordance with process variant (b), compounds of formula I in which R¹ is hydrogen can be manufactured by decarboxylating carboxylic acids of formula IV. This decarboxylation is preferably carried out by dry heating the carboxylic acid of formula IV, which may be crude, to temperatures of about 150° C. to about 400° C., the temperature depending on the melting point of the particular compound of formula IV used.

In accordance with process variant (c), compounds of formula I in which R¹ is halogen can be manufactured by halogenating compounds of formula Ia. Suitable halogenating agents are, for example, N-chlorosuccinimide, N-bromosuccinimide, N-chloroacetamide, N-bromoacetamide and elemental iodine. As solvents there are conveniently used inert organic solvents, for example halogenated hydrocarbons such as methylene chloride, 1,2-dichloroethane, chloroform and the like, dimethylformamide, dimethylacetamide, acetonitrile, ethers such as diethyl ether, tetrahydrofuran, dioxan and the like, etc. The halogenation can be carried out in a temperature range of about 0° C. to about 120° C. depending on the solvent used.

In accordance with process variant (d), compounds of formula I in which R¹ is lower alkoxymethyl can be manufactured by etherifying an alcohol of formula Va with an alkylating agent yielding the desired lower alkyl group or etherifying a compound of formula VIa with a lower alcohol. This etherification is carried out in an inert organic solvent such as dimethylformamide, hexamethylphosphoric acid triamide, dimethyl sulphoxide, tetrahydrofuran or any other suitable organic solvent and in the presence of a base which is sufficiently strongly basic to form the corresponding alcoholate from the alcohol of formula Va or from the lower alcohol. Suitable bases are, for example, alkali metal hydrides such as sodium hydride, alkali metals such as sodium and alkali metal amides such as lithium amide and lithium diisopropylamide. Suitable alkylating agents are, for example, halides such as methyl iodide, ethyl bromide and ethyl iodide and dialkyl sulphates such as dimethyl sulphate and diethyl sulphate. This etherification is conveniently carried out at a temperature between about 0° C. and about 50° C.

In accordance with process variant (e), compounds of formula I in which $R^1$ is lower alkyl can be manufactured by cleaving off under reductive conditions the leaving group denoted by Z' in a compound of formula VI. This process variant is carried out according to methods known per se, the choice of the suitable leaving group denoted by Z' as well as the determination of the conditions suitable for the cleavage, under which other structural elements present in the molecule should not be affected, presenting no difficulties to a person skilled in the art. Especially suitable leaving groups for the present process aspect are, for example, halogen atoms such as chlorine, bromine and iodine, which can be cleaved off readily under hydrogenolytic conditions, for example by treatment with elemental hydrogen in the presence of a suitable catalyst (e.g. palladium/carbon, Raney/nickel, etc.) in an inert organic solvent. Suitable solvents are, for example, alcohols such as methanol, ethanol and isopropanol, ethers such as diethyl ether, tetrahydrofuran, dioxan and dimethoxyethane, and the like. Depending on the reactivity of the catalyst used the cleavage is carried out at pressures of about normal pressure to about 300 bar and at temperatures of about room temperature to about 150° C.

In accordance with process variant (f), compounds of formula I can be manufactured by trans-esterifying compounds of formula Ic, i.e. by replacing the alkyl group denoted by $R^3$ in a compound of formula Ic by a different group $R^3$.

This trans-esterification is carried out in a manner known per se by reacting a compound of formula Ic with an alcohol corresponding to the desired group denoted by $R^3$ (e.g. with methanol, ethanol or isopropanol) at room temperature or while heating to a temperature of about 25° to 150° C.

Preferably, this trans-esterification is carried out in the presence of a base, with potassium cyanide or similar weak bases being especially suitable in the present case. As the base there is, however, also suitable the alcoholate corresponding to the desired group denoted by $R^3$, for example sodium methanolate, ethanolate or isopropanolate or the corresponding potassium salts. As the solvent there is preferably used the alcohol corresponding to the group denoted by $R^3$ in the desired end compound of formula I. However, the trans-esterification can also be carried out in an inert organic solvent, for example an aromatic hydrocarbon such as benzene or xylene, an ether such as dioxan, tetrahydrofuran or ethyleneglycol dimethyl ether, dimethylformamide, dimethyl sulphoxide or the like. In this trans-esterification not only can a low boiling alcohol be replaced by a high boiling alcohol, but also a high boiling alcohol can be replaced by a low boiling alcohol.

The trans-esterification can, however, also be carried out readily in several stages; for example, by hydrolyzing the compound of formula Ic (as described below) to the corresponding free carboxylic acid of formula IV, preparing from this a reactive functional derivative (e.g. an acid chloride or the like) and subsequently reacting this reactive carboxylic acid derivatives with the alcohol corresponding to the significance of $R^3$ in the desired compound of formula I. This procedure is especially suitable when a t-butyl ester is desired or when $R^3$ is t-butyl in a compound of formula Ic.

In accordance with process variant (g), compounds of formula Ib can be converted into corresponding compounds of formula I in which X is a sulphur atom by treatment with a sulphurizing agent, which can be carried out in a manner known per se. For example, the sulphurizing agent can be phosphorus pentasulphide, this being preferably used in excess and the reaction being advantageously carried out in an inert organic solvent such as dioxan, methylene chloride or the like in the presence of triethylamine at a temperature of about 50° C. up to the reflux temperature of the reaction mixture. Other suitable sulphurizing agents are compounds such as 2,4-bis(p-methoxyphenyl)-1,3,2,4-dithiaphosphetane-2,4-disulphide; such sulphurizing agents being used in approximately the calculated amount and the reaction being carried out in the presence of an inert solvent such as toluene or xylene, conveniently at the reflux temperature of the reaction mixture, or in hexamethylphosphoric acid triamide at a temperature between about 60° and 110° C.

In accordance with process variant (h), compounds of formula I can be converted into pharmaceutically acceptable acid addition salts. The manufacture of such pharmaceutically acceptable acid addition salts is carried out according to generally usual methods. The salts provided by the present invention are salts formed with inorganic acids and with organic acids; for example, hydrochlorides, hydrobromides, sulphates, methanesulphonates, p-toluenesulphonates, oxalates and the like.

The compounds of formula II used as starting materials can be prepared starting from compounds of the formula

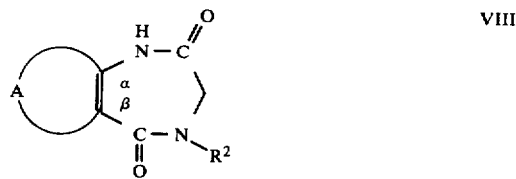

VIII wherein A and $R^2$ are as above, according to methods which are known per se; see, for example, Belgian Patent Specifications Nos. 802 233, 833 249 and 865 653, U.S. Pat. No. 3,681,341 and J. Org. Chemistry 29, 231 (1964) incorporated herein by reference.

Various Examples hereinafter contain detailed information concerning the preparation of compounds of formula II from compounds of formula VIII.

The compounds of formula VIII, in turn, can be prepared readily according to methods known per se; for example, in accordance with Formula Scheme 1 hereinafter in which A' is the group (a) or (b), A" is the group (c) or (d) and $R^2$ is as above:

Formula Scheme 1

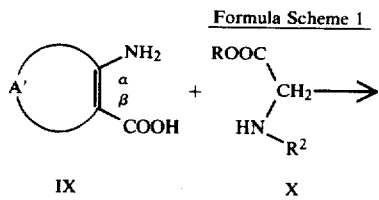

IX        X

-continued
Formula Scheme 1

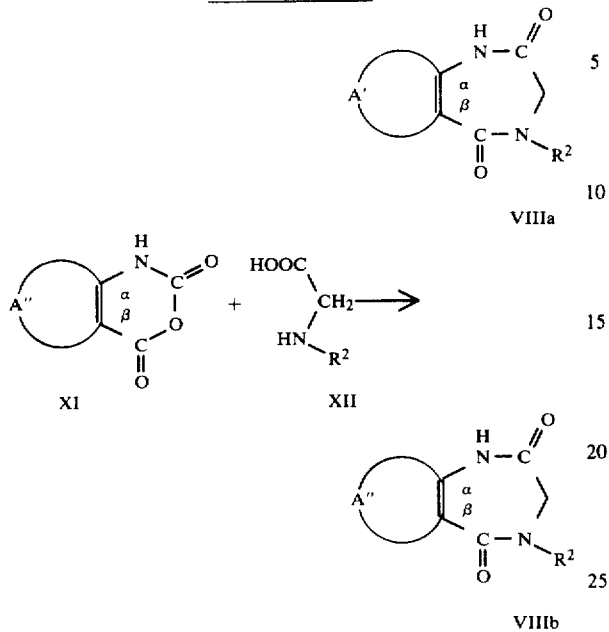

The reaction of a compound of formula IX with a compound of formula X is carried out in the presence of N,N'-carbonyldiimidazole in an inert organic solvent such as dimethylformamide, tetrahydrofuran, dioxan or the like. The reaction is preferably carried out in a "one-pot process", i.e. the carboxylic acid imidazolide formed in a first step is not isolated, but is reacted directly with a compound of formula X to give a compound of formula VIIIa.

The reaction of a compound of formula XI with an amino acid of formula XII to give a compound of formula VIIIb is carried out in an inert organic solvent such as dimethyl sulphoxide, dimethylformamide or the like in a temperature range of about 50° C. to about 200° C.

The carboxylic acids of formula IV used as starting materials can be prepared by hydrolyzing the ester group in a compound of formula Ic. This hydrolysis is carried out according to methods which are known per se and familiar to any person skilled in the art. If the compound of formula Ic is a tertiary alkyl ester (e.g. a t-butyl ester), then the hydrolysis is conveniently carried out in acidic solution. Acids which can be used in this case are trifluoroacetic acid, concentrated or dilute mineral acids such as hydrochloric acid, hydrobromic acid, phosphoric acid and the like, etc. The hydrolysis is conveniently carried out at an elevated temperature, for example at the boiling point of the mixture or slightly thereunder. In the remaining cases the hydrolysis is conveniently carried out using an aqueous alkali such as sodium hydroxide and potassium hydroxide, optionally in the presence of a solubilizer. Suitable solubilizers are alcohols such as methanol and ethanol, ethers such as tetrahydrofuran and dioxan, and the like. The alkaline hydrolysis is preferably carried out in a temperature range of about room temperature to the boiling point of the mixture.

The compounds of formula Va used as starting materials can be prepared, for example, by reducing carboxylic acid esters of formula Ic. The reduction is preferably carried out using a reducing agent such as lithium borohydride in an inert organic solvent such as diethyl ether, tetrahydrofuran, dimethoxyethane or the like.

The compounds of formula VI used as starting materials can be prepared readily from compounds of formula Va in accordance with Formula Scheme 2 hereinafter in which A, X, Z' and $R^2$ are as above and $R^{51}$ is lower alkyl:

Formula Scheme 2

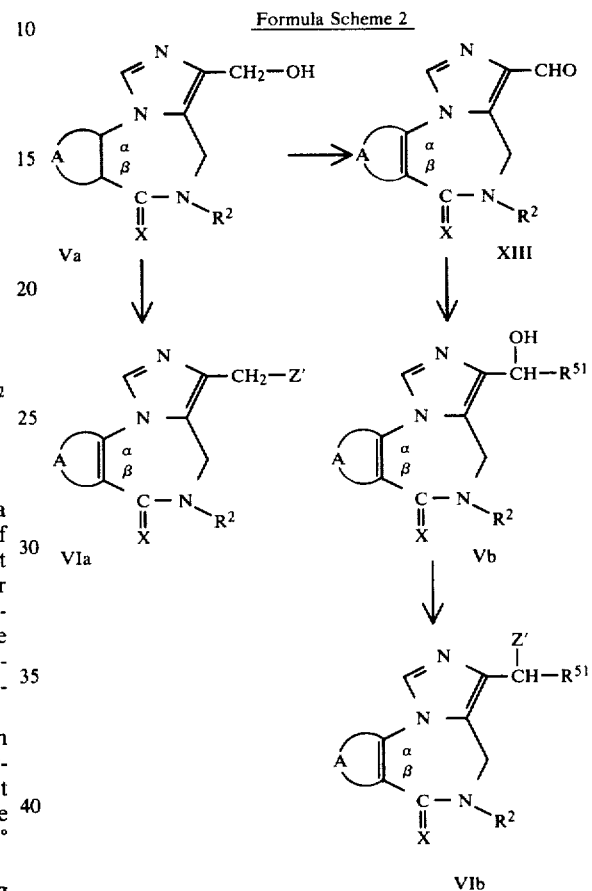

The preparation of a compound of formula XIII from an alcohol of formula Va is preferably carried out using a mild oxidizing agent such as manganese dioxide or the like in an inert organic solvent such as methylene chloride, chloroform or the like.

The compounds of formula Vb can be prepared by reacting a compound of formula XIII with a metal-organic compound yielding the group $R^{51}$ according to methods which are generally known and familiar to any person skilled in the art. Preferred metal-organic compounds are Grignard compounds such as methyl-magnesium iodide, ethyl-magnesium iodide, isopropyl-magnesium bromide, n-propyl-magnesium bromide, n-butyl-magnesium chloride and the like. Suitable solvents are ethers such as diethyl ether, tetrahydrofuran, t-butyl methyl ether, mixtures thereof, and the like. Conveniently, the reaction is carried out at the boiling point of the reaction mixture, although it can, however, also be carried out at a lower temperature (e.g. at room temperature).

The compounds of formula VI (i.e. formulae VIa and VIb) can be prepared from compounds of formula Va or Vb according to methods which are generally known and familiar to any person skilled in the art. Corresponding halides are obtained, for example, by treating compounds of formula Va or Vb with halogenating agents such as thionyl chloride, phosphorus oxychloride, phosphorus pentachloride, carbon tetrabromide/triphenylphosphine and the like.

The compounds of formulae II, IV, Va and VI used as starting materials are novel and are likewise objects of the present invention.

As mentioned earlier, the compounds of formula I are novel and have extremely valuable pharmacodynamic properties. They exhibit only a low toxicity and it has been shown that they have a pronounced affinity to the central benzodiazepine receptors and are capable of antagonizing the central-depressant, muscle relaxant, ataxic, blood pressure-lowering and respiratory-depressant properties of 1,4-benzodiazepines which have tranquillizing activity.

The affinity of compounds of formula I to the central benzodiazepine receptors was determined according to the method described in Life Science 20, 2101-2110 (1977) and Science 198, 849-851 (1977). According to this method, the inhibition of the binding or tritiated diazepam as the specific benzodiazepine receptors in the cerebral cortex by the respective test substances is ascertained. The $IC_{50}$ ("50% inhibiting concentration") is that concentration of the respective test substances which brings about a 50 percent inhibition of the specific binding of the tritiated diazepam at the specific benzodiazepine receptors in the cerebral cortex.

One of the typical properties of 1,4-benzodiazepines, which have tranquillizing activity, in experimental animals is their pronounced anticonvulsant activity which can be demonstrated, for example, in the known and generally recognized pentetrazole test. This property was used to evaluate the test described hereinafter which permits the determination of compounds which are capable of antagonizing the central properties of 1,4-benzodiazepines which have tranquillizing activity.

In this test, 5 mg/kg (i.p.) of diazepam (i.e. a supramaximal dosage which in the pentetrazole test on more than 900 mice protects all experimental animals from convulsive attacks) are administered to mice 1 hour before the pentetrazole (120 mg/kg, i.p.) and the compound to be tested was administered p.o. or i.v. 15 minutes before the pentetrazole. The antagonistic activity of the compounds investigated, i.e. their ability to counteract the activity of the diazepam in the pentetrazole test, is determined by counting the mice which suffer convulsive attacks in this test.

In the following Table there are presented the results which have been obtained with representative members of the class of compound defined by formula I in the test previously described. The $ED_{50}$ value is given for each compound listed in the Table. The $ED_{50}$ is the amount of test compound in mg/kg (p.o. or i.v.) which counteracts in 50% of the animals the diazepam effect in the above test. Moreover, the Table contains the $IC_{50}$ value (defined above) for all test compounds listed therein.

TABLE

| Compound of formula I | | | | $IC_{50}$ | $ED_{50}$ in mg/kg | |
|---|---|---|---|---|---|---|
| A  Rhu 1 | $R^2$ | $R^3$ | X | in nM/l | p.o. | i.v. |
| (b) —COOC(CH$_3$)$_3$ | H | —CH$_3$ | O | 3.0 | 0.23 | 0.16 |
| (b) —COOCH$_2$CH$_3$ | H | —CH$_3$ | O | 7.0 | 1.94 | — |
| (a) —COOC(CH$_3$)$_3$ | H | —CH$_3$ | O | 17.0 | 5.4 | 3.1 |
| (d) —COOC(CH$_3$)$_3$ | H | —CH$_3$ | O | 130 | 15.1 | — |

As mentioned earlier, the compounds of formula I antagonize the central-depressant, muscle relaxant, ataxic, blood pressure-lowering and respiratory-depressant properties of 1,4-benzodiazepines which have tranquillizing activity. The latter are in widespread use in therapy and are often administered in high dosages, so that the above-mentioned activities can also appear strongly as side-effects. The compounds of formula I can be used as antidotes in the case of intoxications in which excessive intake of 1,4-benzodiazepines which have tranquillizing activity is concerned. They are also suitable for shortening anaesthesia in surgery and in obstetrics induced by 1,4-benzodiazepines which have tranquillizing activity. In the case of neonatals, a possible respiratory depression, which deteriorates upon the administration of 1,4-benzodiazepines which have tranquillizing activity to the mother, can be counteracted. The compounds of formula I can also be used to suppress, in the case of 1,4-benzodiazepines which are used in other fields of indication, the activities on the central nervous system which are undesirable in such a case. Examples of such 1,4-benzodiazepines which can be used in other fields of indication are the schistosomicidally-active 1,4-benzodiazepines described in British Patent Specifications Nos. 1,444,529 and 1,474,305 (incorporated herein by reference) such as (+)-5-(o-chlorophenyl)-1,3-dihydro-3-methyl-7-nitro-2H-1,4-benzodiazepin-2-one.

The compounds of formula I and their pharmaceutically acceptable acid addition salts can be used as medicaments, for example in the form of pharmaceutical preparations. The pharmaceutical preparations can be administered orally (e.g. in the form of tablets, coated tablets, dragées, hard and soft gelatine capsules, solutions, emulsions or suspensions). The administration can, however, also be carried out rectally (e.g. in the form of suppositories) or parenterally (e.g. in the form of injection solutions).

For the manufacture of tablets, coated tablets, dragées and hard gelatine capsules, the compounds of formula I and their pharmaceutically acceptable acid addition salts can be processed with pharmaceutical inert, inorganic or organic carriers. Examples of such carriers which can be used for tablets, dragées and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols etc. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils etc. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, compounds of formula I and pharmaceutically acceptable acid addition salts thereof can be used in the control or prevention of illnesses, especially in the antagonization of the central-depressant, muscle relaxant, ataxic blood pressure-lowering and respiratory-depressant properties of 1,4-benzodiazepines which have tranquillizing activity. In particular, compounds of formula I can be used in combination with the schistosomicidally-active compounds mentioned above, for exampe in combination with (+)-5-(o-chlorophenyl)-1,3-dihydro-3-methyl-7-nitro-2H-1,4-benzodiazepin-2-one, in the control of schistosomiasis. In this case, the compounds of formula I or their pharmaceutically acceptable acid addition salts can be administered before, simultaneously with or after the administration or intake of 1,4-benzodiazepines which have tranquillizing activity. If the compound of formula I or a pharmaceutically acceptable acid addition salt thereof is administered simultaneously with the 1,4-benzodiazepine which has tranquillizing activity, then the administration can be as an ad-hoc combination or in the form of a pharmaceutical combination which contains a compound of formula I or a pharmaceutically acceptable acid addition salt thereof and a 1,4-benzodiazepine derivative which has tranquillizing activity; such pharmaceutical combinations are likewise an object of the present invention. The dosage of the compounds of formula I and their pharmaceutically acceptable acid addition salts can vary within wide limits and is, of course, fitted to the individual requirements in each particular case. In general, a daily dosage of about 0.2 to about 500 mg should be appropriate.

As mentioned earlier, medicaments containing a compound of formula I or a pharmaceutically acceptable acid addition salt thereof are likewise an object of the present invention as is a process for the manufacture of such medicaments which comprises bringing one or more compounds of formula I or pharmaceutically acceptable acid addition salts thereof and, if desired, one or more other therapeutically valuable substances into a galenical administration form; in this connection reference is again made to the pharmaceutical combinations mentioned above which are likewise an object of the present invention. In particular, pharmaceutical combinations containing a compound of formula I and one of the schistosomicidally-active compounds mentioned above, especially (+)-5-(o-chlorophenyl)-1,3-dihydro-3-methyl-7-nitro-2H-1,4-benzodiazepin-2-one, are an object of the present invention. Such combinations are suitable for the control of schistosomiasis.

In the following Examples, which illustrate the present invention in more detail but in no way are intended to limit its extent, all temperatures are given in degrees Centigrade.

EXAMPLE 1

(a) 5.52 g (40 mmol) of 4-aminonicotinic acid in 50 ml of dimethylformamide are treated with 6.48 g (40 mmol) of N,N'-carbonyldiimidazole and the mixture is stirred at 50° for 2.5 hours. Subsequently, there are added to the mixture obtained 4.04 g (40 mmol) of triethylamine and 6.22 g (40 mmol) of methyl sarcosinate hydrochloride and the resulting mixture is stirred at 80° for 2 hours and at the boiling point for 3.5 hours. After removing the dimethylformamide in vacuo, the crude product obtained is purified by column chromatography on silica gel and subsequent recrystallization from ethanol. There is obtained 3,4-dihydro-4-methyl-2H-pyrido[4,3-e][1,4]diazepine-2,5(1H)-dione of melting point 267°–268°.

(b) 3.33 g (17.4 mmol) of 3,4-dihydro-4-methyl-2H-pyrido[4,3-e][1,4]diazepine-2,5(1H)-dione in 35 ml of dimethylformamide are treated with 450 mg (18.8 mmol) of sodium hydride oil dispersion washed with hexane, the mixture is stirred at room temperature for 30 minutes, there are subsequently added dropwise thereto at −20° 3.0 g (1.4 mmol) of diethylchlorophosphate and the mixture is stirred at −20° for 20 minutes.

Separately, a solution of 1.96 g (17.5 mmol) of potassium t-butylate in 4 ml of dimethylformamide is cooled to about −50°, treated with 2.64 g (17.4 mmol) of t-butyl isocyanoacetate and added dropwise at −10° to −30° to the mixture obtained according to the preceding paragraph. The cooling is removed, the mixture is stirred for a further 20 minutes, poured into about 200 ml of water and extracted with chloroform. The combined chloroform extracts are washed with water, dried over magnesium sulphate and evaporated. By column chromatography on silica gel and subsequent recrystallization from ethyl acetate there is obtained t-butyl 5,6-dihydro-5-methyl-6-oxo-4H-imidazo[1,5-a]pyrido[3,4-f][1,4]diazepine-3-carboxylate of melting point 214°–215°.

EXAMPLE 2

(a) A suspension of 5.18 g (37.5 mmol) of 3-aminopicolinic acid in 100 ml of dimethylformamide is treated with 6.20 g (38.2 mmol) of N,N'-carbonyldiimidazole and the mixture is stirred at room temperature for 1 hour. To the light brown solution obtained there are added 3.84 g (38 mmol) of triethylamine and 5.30 g (38 mmol) of methyl sarcosinate hydrochloride and the mixture is stirred at the boiling point for 6 hours. After removing the dimethylformamide in vacuo, the residue is crystallized from ethanol. There is obtained 3,4-dihydro-4-methyl-2H-pyrido[3,2-e][1,4]diazepine-2,5(1H)-dione of melting point 272°–274°.

(b) 3 g (15.7 mmol) of 3,4-dihydro-4-methyl-2H-pyrido[3,2-e][1,4]diazepine-2,5(1H)-dione in 20 ml of dimethylformamide are treated with 0.61 g (15.9 mmol) of sodium hydride (60 percent oil dispersion), the mixture is stirred at room temperature for 1 hour, there are subsequently added dropwise thereto at 20° 2.72 g (15.8 mmol) of diethylchlorophosphate and the mixture is stirred at 20° for a further 20 minutes.

Separately, a solution of 1.77 g (15.8 mmol) of potassium t-butylate in 3 ml of dimethylformamide is cooled to −50° and treated with 2.28 g (15.8 mmol) of t-butyl isocyanoacetate. The orange solution obtained is added dropwise at −10° to −20° to the mixture obtained according to the preceding paragraph. The cooling is removed, the mixture is stirred for a further 20 minutes, neutralized with acetic acid, poured into water and extracted with chloroform. The combined chloroform extracts are washed with water, dried over magnesium sulphate and evaporated. By column chromatography on silica gel and subsequent recrystallization from ethyl acetate there is obtained t-butyl 5,6-dihydro-5-methyl-6-oxo-4H-imidazo[1,5-a]pyrido[2,3-f][1,4]diazepine-3-carboxylate of melting point 234°–236°.

EXAMPLE 3

A suspension of 1.51 g (34.5 mmol) of sodium hydride (55 percent oil dispersion) in 40 ml of dry dimethylformamide is treated with 6.0 g (31.4 mmol) of 3,4-dihydro-4-methyl-2H-pyrido[3,2-e][1,4]diazepine-2,5(1H)-dione, the mixture is stirred at room temperature for 45 minutes, subsequently cooled to −35°, treated dropwise with 5.0 ml (34.5 mmol) of diethylchlorophosphate and the resulting mixture is stirred at −30° to −15° for 10 minutes.

Separately, a solution of 3.86 g (34.5 mmol) of potassium t-butylate in 8 ml of dry dimethylformamide is cooled in an acetone/dry-ice bath, treated with 3.8 ml (34.5 mmol) of ethyl isocyanoacetate and added dropwise at $-15°$ to the mixture obtained according to the preceding paragraph. The cooling bath is removed, the mixture is stirred at $-15°$ to 5° for about 15 minutes, neutralized with glacial acetic acid, poured into 150 ml of water and extracted three times with chloroform. The chloroform extracts are washed once with saturated sodium chloride solution, dried over magnesium sulphate and evaporated. The crude product obtained is chromatographed on silica gel using chloroform/methanol (19:1) for the elution and subsequently crystallized from ethyl acetate. There is obtained ethyl 5,6-dihydro-5-methyl-6-oxo-4H-imidazo[1,5-a]pyrido[2,3-f][1,4]diazepine-3-carboxylate of melting point 252°–254°.

EXAMPLE 4

(a) A mixture of 1.61 g (5.6 mmol) of ethyl 5,6-dihydro-5-methyl-6-oxo-4H-imidazo[1,5-a]pyrido[2,3-f][1,4]-diazepine-3-carboxylate, 0.33 g (8.2 mmol) of sodium hydroxide, 9 ml of water and 27 ml of ethyl alcohol is heated to boiling under reflux for 25 minutes. The mixture is treated with 8.2 ml of 1 N hydrochloric acid, the ethanol is removed by distillation, the residue is diluted with water and left to stand in an ice-bath for 1 hour. The precipitated material is filtered off under suction, washed with water and dried. There is obtained 5,6-dihydro-5-methyl-6-oxo-4H-imidazo[1,5-a]pyrido[2,3-f][1,4]diazepine-3-carboxylic acid of melting point 292°–295°.

(b) 1.0 g (3.9 mmol) of 5,6-dihydro-5-methyl-6-oxo-4H-imidazo[1,5-a]pyrido[2,3-f][1,4]diazepine-3-carboxylic acid are heated with a Bunsen burner until the gas evolution has ceased. Subsequently, the crude product is chromatographed on silica gel using chloroform/methanol (4:1) for the elution and subsequently crystallized from ethyl acetate. There is obtained 4,5-dihydro-5-methyl-6H-imidazo[1,5-a]pyrido[2,3-f][1,4]diazepin-6-one of melting point 199°–201°.

EXAMPLE 5

0.56 g (2.6 mmol) of 4,5-dihydro-5-methyl-6H-imidazo[1,5-a]pyrido[2,3-f][1,4]diazepin-6-one and 0.35 g (2.6 mmol) of N-chlorosuccinimide are treated with 10 ml of dimethylformamide and the mixture is stirred at 90°–100° for 30 minutes. After evaporation to dryness, the residue is chromatographed on silica gel using chloroform containing 4% methanol for the elution. After recrystallization from ethyl acetate, there is obtained 3-chloro-4,5-dihydro-5-methyl-6H-imidazo[1,5-a]pyrido[2,3-f][1,4]diazepin-6-one of melting point 247°–248°.

EXAMPLE 6

(a) 12.0 g (73.1 mmol) of 3-azaisatoic acid anhydride and 6.6 g (73.2 mmol) of sarcosine are stirred at 100° for 2.5 hours in 180 ml of dimethyl sulphoxide. The solvent is removed in a high vacuum and the oily residue is heated to 130° for about 4 hours. After cooling, the crystalline product is suspended in 150 ml of methanol. It is filtered off under suction, washed with methanol and dried. There is obtained 3,4-dihydro-4-methyl-2H-pyrido[2,3-e][1,4]diazepine-2,5(1H)-dione of melting point 245°–247°.

(b) A suspension of 1.39 g (31.9 mmol) of sodium hydride (55 percent oil dispersion) in 40 ml of dry dimethylformamide is treated with 5.3 g (27.7 mmol) of 3,4-dihydro-4-methyl-2H-pyrido[2,3-e][1,4]diazepine-2,5(1H)-dione, the mixture is stirred at room temperature for 30 minutes, cooled to $-35°$, treated dropwise with 4.8 ml (31.9 mmol) of diethylchlorophosphate and the mixture is stirred at $-35°$ to $-15°$ for 15 minutes.

Separately, a solution of 3.7 g (33.2 mmol) of potassium t-butylate in 10 ml of dry dimethylformamide is cooled in an acetone/dry-ice bath and treated with 4.65 g (33.2 mmol) of t-butyl isocyanoacetate. The thus-obtained solution is added dropwise at $-15°$ to the mixture obtained according to the preceding paragraph. Subsequently, the cooling is removed, the mixture is stirred for a further 1 hour, neutralized with 1.9 ml of glacial acetic acid and evaporated to dryness in a high vacuum. The residue is chromatographed on silica gel using chloroform/methanol (19:1) for the elution and subsequently recrystallized from ethyl acetate. There is obtained t-butyl 5,6-dihydro-5-methyl-6-oxo-4H-imidazo[1,5-a]pyrido[3,2-f][1,4]diazepine-3-carboxylate of melting point 150°–151°.

EXAMPLE 7

6.9 g (36.1 mmol) of 3,4-dihydro-4-methyl-2H-pyrido[4,3-e][1,4]benzodiazepine-2,5(1H)-dione are added to a stirred suspension of 1.81 g (41.5 mmol) of sodium hydride (55 percent oil dispersion) in 45 ml of dry dimethylformamide and the mixture is left to stir for 1 hour. Subsequently, there are added dropwise thereto at $-30°$ 6.0 ml (41.5 mmol) of diethylchlorophosphate.

Separately, a solution of 4.85 g (43.3 mmol) of potassium t-butylate in 10 ml of dry dimethylformamide is cooled in an acetone/dry-ice bath, treated with 4.8 ml (43.3 mmol) of ethyl isocyanoacetate and added dropwise at $-15°$ to $-20°$ to the mixture obtained according to the preceding paragraph. The cooling bath is removed, the mixture is stirred for 20 minutes, neutralized with glacial acetic acid, poured into 100 ml of water and extracted six times with methylene chloride. The methylene chloride solution is dried over magnesium sulphate and evaporated. The crude product is chromatographed on silica gel using chloroform/methanol (19:1) for the elution. Two-fold recrystallization of the material obtained from ethyl acetate yields ethyl 5,6-dihydro-5-methyl-6-oxo-4H-imidazo[1,5-a]pyrido[3,4-f][1,4]diazepin-3-carboxylate of melting point 205°–206°.

t-Butyl 5,6-dihydro-5-methyl-6-oxo-4H-imidazo[1,5-a]pyrido[3,4-f][1,4]diazepine-3-carboxylate (active substance A) can be used as the active substance for the manufacture of pharmaceutical preparations as illustrated in Examples A to G:

EXAMPLE A

Tablets containing the following ingredients are manufactured in the usual manner:

|  | mg/tablet |
| --- | --- |
| Active substance A | 1 |
| Lactose | 103 |
| Maize starch | 25 |
| Microcrystalline cellulose | 70 |
| Magnesium stearate | 1 |
| Total | 200 |

EXAMPLE B

Capsules containing the following ingredients are manufactured:

|  | mg/capsule |
|---|---|
| Active substance A | |
| Lactose | 164 |
| Maize starch | 30 |
| Talc | 5 |
| Total | 200 |

The active substance, lactose and maize starch are firstly mixed in a mixer and then in a comminuting machine. The mixture is returned to the mixer, the talc is added thereto and mixed thoroughly. The mixture is filled by machine into hard gelatine capsules.

EXAMPLE C

Injection solutions containing the following ingredients are manufactured:

|  | Per ml |
|---|---|
| Active substance A | 2.5 mg |
| D-(−)-Mannitol | 52 mg |
| Water for injection q.s. ad | 1.0 ml |

For the manufacture of 10 000 ml of injection solution, 520 g of D-(−)-mannitol are dissolved in 9000 ml of water for injection. Then, 25 g of the active substance are dissolved in the resulting solution and the solution thus obtained is made up to 10 000 ml with water for injection. This solution is filtered and filled into ampoules of suitable size; the residual volume of the ampoules is filled with nitrogen, the ampoules are sealed and they are sterilized, for example at 120° for 20 minutes.

EXAMPLE D

Suppositories containing the following ingredients are manufactured:

|  | g/supp. |
|---|---|
| Active substance A | 0.001 |
| Cocoa butter (m.p. 36–37°) | 1.255 |
| Carnauba wax | 0.044 |
| Total | 1.3 |

The cocoa butter and carnauba wax are melted in a glass or steel vessel, mixed thoroughly and cooled to 45°. Thereupon, there is added thereto the finally powdered active substance and the mixture is stirred until it is completely dispersed. The mixture is poured into suppository moulds of suitable size, left to cool, the suppositories are removed from the moulds and packed individually in wax paper or metal foil.

EXAMPLE E

Capsules containing the following ingredients are manufactured:

|  | mg/capsule |
|---|---|
| Active substance A | 20.0 |
| (+)-5-(o-Chlorophenyl)-1,3-dihydro-3-methyl-7-nitro-2H—1,4-benzodiazepin-2-one (active substance B) | 30.0 |
| Lactose (crystalline) | 100.0 |
| Maize starch (white) | 27.5 |
| Talc | 10.0 |
| Magnesium stearate | 2.5 |
| Total | 190.0 |

The two active substances are mixed well with the adjuvants and 190.0 mg of the mixture are filled into interlocking capsules of suitable size.

EXAMPLE F

Tablets containing the following ingredients are manufactured:

|  | mg/tablet |
|---|---|
| Active substance A | 10.0 |
| (+)-5-(o-Chlorophenyl)-1,3-dihydro-3-methyl-7-nitro-2H—1,4-benzodiazepin-2-one (active substance B) | 30.0 |
| Lactose (powdered) | 15.0 |
| Maize starch (white) | 19.5 |
| Povidon K30 | 3.5 |
| Maize starch (white) | 10.0 |
| Magnesium stearate | 2.0 |
| Total | 90.0 |

The two active substances, the powdered lactose and the first portion of white maize starch are mixed and sieved. This mixture is moistened with a solution of the Povidon K30 in water, kneaded, granulated, dried and seived. The second portion of white maize starch and the magnesium stearate are added to the granulate. After mixing, the mass obtained is pressed to tablets weighing 90 mg.

EXAMPLE G

Tablets containing the following ingredients are manufactured:

|  | mg/tablet |
|---|---|
| Active substance A | 30 |
| (+)-5-(o-Chlorophenyl)-1,3-dihydro-3-methyl-7-nitro-2H—1,4-benzodiazepin-2-one (active substance B) | 30 |
| Lactose (powdered) | 22 |
| Maize starch (white) | 22 |
| Povidon K30 | 6 |
| Maize starch (white) | 16 |
| Magnesium stearate | 4 |
| Total | 130 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 130 mg.

What is claimed is:

1. A compound of the formula

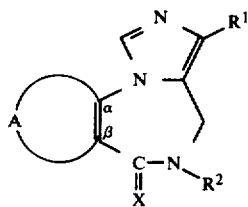

wherein A together with the two carbon atoms denoted as α and β is a pyridine ring, X is an oxygen or sulphur atom, $R^1$ is hydrogen, halogen, lower alkyl, lower alkoxymethyl or a group of the formula —$COOR^3$ and $R^2$ and $R^3$ each are lower alkyl, and pharmaceutically acceptable acid addition salts thereof.

2. The compound of claim 1, wherein $R^1$ is chlorine or the group —$COOR^3$ in which $R^3$ is methyl, ethyl, isopropyl or t-butyl.

3. The compound of claim 2, wherein $R^1$ is the group —$COOR^3$ in which $R^3$ is ethyl or t-butyl.

4. The compound of claim 3, wherein A together with the two carbon atoms denoted as α and β is the group

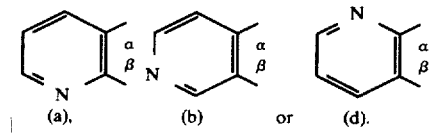

5. The compound of claim 4, wherein A is group (b).
6. The compound of claim 5, wherein $R^2$ is methyl.
7. The compound of claim 6, wherein X is an oxygen atom.
8. The compound: t-Butyl 5,6-dihydro-5-methyl-6-oxo-4H-imidazo-[1,5-a]pyrido[3,4-f][1,4]diazepine-3-carboxylate.

9. The compound: Ethyl 5,6-dihydro-5-methyl-6-oxo-4H-imidazo[1,5-a]-pyrido[3,4-f][1,4]diazepine-3-carboxylate.

10. A compound selected from the group consisting of t-Butyl, 5,6-dihydro-5-methyl-6-oxo-4H-imidazo-[1,5-a]pyrido[2,3-f][1,4]diazepine-3-carboxylate, ethyl 5,6-dihydro-5-methyl-6-oxo-4H-imidazo[1,5-a]pyrido[2,3-f]-[1,4]diazepine-3-carboxylate, 3-chloro-4,5-dihydro-5-methyl-6H-imidazo[1,5-a]pyrido[2,3-f][1,4]diazepin-6-one and t-butyl 5,6-dihydro-5-methyl-6-oxo-4H-imidazo[1,5-a]-pyrido[3,2-f][1,4]diazepine-3-carboxylate.

11. A method of antagonizing, in a patient, the central-depressant, muscle relaxant, ataxic, blood pressure lowering and respiratory-depressant properties of 1,4-benzodiazepines which have tranquillizing activity which comprises daily administration to said patient of from about 0.2 mg to about 500 mg of a compound of the formula

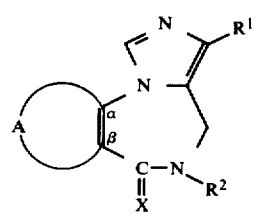

wherein A together with the two carbon atoms denoted as α and β signifies a pyridine ring, X signifies an oxygen or sulphur atom, $R^1$ signifies hydrogen, halogen, lower alkyl, lower alkoxymethyl or the group —$COOR^3$ and $R^2$ and $R^3$ each signify lower alkyl and the pharmaceutically acceptable acid additional salts thereof.

12. The method of claim 11 wherein the 1,4-benzodiazepine also has activity against schistosomiasis.

* * * * *